United States Patent
Park et al.

(10) Patent No.: US 8,496,593 B2
(45) Date of Patent: Jul. 30, 2013

(54) NEEDLE GUIDE

(76) Inventors: Robert Park, Durham, NC (US); Scott P. Jarnagin, Raleigh, NC (US)

( * ) Notice: Subject to any disclaimer, the term of this patent is extended or adjusted under 35 U.S.C. 154(b) by 1051 days.

(21) Appl. No.: 11/712,907

(22) Filed: Mar. 2, 2007

(65) Prior Publication Data

US 2007/0276253 A1 Nov. 29, 2007

Related U.S. Application Data

(63) Continuation-in-part of application No. 11/508,300, filed on Aug. 23, 2006.

(60) Provisional application No. 60/808,552, filed on May 26, 2006.

(51) Int. Cl.
*A61B 8/00* (2006.01)

(52) U.S. Cl.
USPC ............ 600/461; 600/407; 600/437; 600/459

(58) Field of Classification Search
USPC .............................. 600/407, 461, 459; 604/19
See application file for complete search history.

(56) References Cited

U.S. PATENT DOCUMENTS

| | | | |
|---|---|---|---|
| 4,058,001 A | 11/1977 | Waxman | |
| 4,058,114 A | 11/1977 | Soldner | |
| 4,346,717 A | 8/1982 | Haerten | |
| 4,567,896 A | 2/1986 | Barnea | |
| 4,576,175 A | 3/1986 | Epstein | |
| 4,899,756 A | 2/1990 | Somek | |
| 5,095,910 A | 3/1992 | Powers | |
| 5,100,387 A | 3/1992 | Ng | |
| 5,647,373 A | 7/1997 | Paltieli | |
| 5,660,185 A | 8/1997 | Shmulewitz et al. | |
| 5,758,650 A | 6/1998 | Miller et al. | |
| 5,779,675 A * | 7/1998 | Reilly et al. | 604/131 |
| 5,924,992 A | 7/1999 | Park et al. | |
| 6,216,029 B1 | 4/2001 | Paltieli | |
| 6,296,614 B1 | 10/2001 | Pruter | |
| 6,361,499 B1 | 3/2002 | Bates et al. | |
| 6,379,307 B1 | 4/2002 | Filly et al. | |
| 6,475,152 B1 | 11/2002 | Kelly, Jr. et al. | |
| 6,485,426 B2 | 11/2002 | Sandhu | |
| 6,689,067 B2 | 2/2004 | Sauer et al. | |
| 6,695,786 B2 | 2/2004 | Wang | |
| 6,702,749 B2 | 3/2004 | Paladini | |

(Continued)

FOREIGN PATENT DOCUMENTS

| | | |
|---|---|---|
| EP | 1 552 792 A1 | 7/2005 |
| JP | 63-059610 | 4/1988 |

(Continued)

OTHER PUBLICATIONS

International Search Report for PCT/US07/18849, mailed Jul. 14, 2008, 3 pgs.

(Continued)

*Primary Examiner* — Peter Luong

(57) ABSTRACT

A needle guide for an ultrasound guidance system. The needle guide may be included as part of a sterile kit for an ultrasound probe. The kit includes a shell and a sheath which form a sterile cover for the ultrasound probe. The needle guide is used to guide a needle into a body using the ultrasound probe.

13 Claims, 14 Drawing Sheets

U.S. PATENT DOCUMENTS

| | | |
|---|---|---|
| 6,733,458 B1 | 5/2004 | Stems |
| 6,743,177 B2 | 6/2004 | Ito |
| 6,755,789 B2 | 6/2004 | Stringer et al. |
| 6,764,449 B2 | 7/2004 | Lee et al. |
| 6,951,542 B2 | 10/2005 | Greppi et al. |
| 7,087,024 B1 | 8/2006 | Pruter |
| 2002/0123689 A1 | 9/2002 | Furia |
| 2002/0133079 A1 | 9/2002 | Sandhu |
| 2002/0156376 A1 | 10/2002 | Wang et al. |
| 2004/0133111 A1 | 7/2004 | Szczech et al. |
| 2005/0131291 A1 | 6/2005 | Floyd et al. |
| 2006/0064010 A1 | 3/2006 | Cannon, Jr. et al. |
| 2006/0129046 A1 | 6/2006 | Stevens et al. |
| 2006/0241477 A1 | 10/2006 | Sasady et al. |

FOREIGN PATENT DOCUMENTS

| | | |
|---|---|---|
| JP | 2002-102221 A2 | 4/2002 |
| WO | 96/32066 A1 | 10/1996 |
| WO | 00/40155 A1 | 7/2000 |

OTHER PUBLICATIONS

U.S. Appl. No. 11/634,994, filed Dec. 7, 2006, Ultrasonic Probe with a Needle Clip and Method of Using Same, Park.

European Patent Office, Supplementary Search Report for EP Application No. 06802289.6, dated Oct. 8, 2010.

European Patent Office, European Search Report, Amended Abstract and Search Opinion for European Patent Application No. 11150958.4, dated Jun. 28, 2011.

Park, Robert, U.S. Appl. No. 11/534,994 Final Office Action dated Jun. 14, 2011.

Japanese Patent Office, Japanese Office Action for Japanese Patent Application No. P2008-529122, dated Sep. 6, 2011.

European Patent Office, European Official Communication for European Patent Application No. 06 802 289.6 dated Sep. 18, 2012.

* cited by examiner

NEEDLE GUIDE

CROSS REFERENCE AND RELATED APPLICATIONS

This application is a continuation-in-part of pending U.S. application Ser. No. 11/508,300, filed Aug. 23, 2006 by Robert Park, et al., published as U.S. Patent Application Publication No. 2007/0073155, the entire contents of which are incorporated by reference, and to which priority is claimed under 35 U.S.C. §120. This application also claims priority under 35 U.S.C. §119(e) to U.S. Provisional Application No. 60/808,552 filed May 26, 2006.

FIELD

The disclosure relates generally to imaging devices, such as an ultrasound device, and more particularly a sterile cover and needle guide.

BACKGROUND

In a typical ultrasound guided procedure, a doctor will place a small, handheld probe known as a transducer on a patient's skin. The transducer converts electrical energy to acoustic energy. Acoustical energy is transmitted from the transducer and into the patient's body in the form of sound waves. The transmitted sound waves are either reflected back towards the transducer or absorbed by the medium, depending on the acoustical impedance. The reflected sound waves are converted into electrical signals which are used to form a real time two-dimensional image of a portion of the patient's body. This ultrasound image may be used to assist a health professional with locating a point where an invasive medical device, e.g., a needle, is inserted. After locating the correct insertion point, the health professional may then begin the medical procedure, such as insertion of a catheter, administration of a local anesthetic, or removal of tissue as in a biopsy.

Before beginning a procedure, it is necessary to cover the ultrasound device to assure that sterility is maintained during the procedure. Typically, a sterile sleeve or condom made of a flexible, sterilizable material is draped over the device to form a sterility barrier. A sterility barrier is intended to refer to a seal, bond, covering, etc. that is effective in preventing micro-organisms or other contaminates from migrating from within the sleeve, condom, etc. to the exterior, sterile environment. An acoustic coupling gel is placed in the sleeve before placing the transducer in the sleeve to ensure consistent contact between the sound transmitting/receiving end or head of the transducer and the sleeve. This contact is necessary to ensure there are no artifacts in the ultrasound image due to the presence of air pockets between the head and sleeve. The coupling gel may be applied to the sleeve at the time of the procedure or the gel may be pre-applied to the sleeve. In the later case, a breakable seal is usually included in the sleeve to protect the gel from contaminates. This type of cover is described in U.S. Pat. No. 5,676,159. The end opposite the head of the transducer is typically sealed using a rubber band wrapped around the sleeve.

Brackets are sometimes provided with an ultrasound device for purposes of mounting a needle guide. The needle guide is used to facilitate a longitudinal or transverse type ultrasound guided needle insertion procedure. In the "transverse" type, the guide is arranged so that the needle is inserted into the patient along a plane transverse to the ultrasound image plane. In the "longitudinal" type, the needle is inserted into the patient in a plane parallel to the ultrasound image plane.

One known ultrasound device for assisting a health professional with needle placement in a body is the ilook™ personal imaging tool, sold by SonoSite®, Inc., which includes a series of removable needle guides and a bracket for mounting the needle guides to the transducer. The device is used to place a needle at a target beneath the skinline by real-time visual identification of the target via an ultrasonic image. The needle guide is arranged on the transducer so that a needle received therein will extend approximately perpendicular to the sonic scanning plane. Thus, the SonoSite®, Inc. device is a transverse-type device. A sterile needle guide is snap-fit on the bracket. There is more than one-type of needle guide to choose from. The choice depends upon the distance between the skinline and the needle's target in the body. The needle guide has a door that can be locked in a closed position by a slidable switch, thereby retaining the needle shaft between the door and a semi-circular recessed area. The needle is placed in this recessed area and the door is closed to hold the needle therein. The transducer with needle is then placed on the skinline and the top of the vessel is located via the sonic image. The needle is then inserted into the body. After the needle has reached the target, the transducer is removed from the needle, which requires a manual unlatching of the door of the needle guide. A related needle guide is described in U.S. Publication No. 2005/0131291.

SUMMARY

The disclosure is directed to a sterile cover and needle guide for an ultrasound probe. According to one aspect of the disclosure, the needle guide is operated by applying finger pressure to the guide so as to retain a needle shaft in the guide. When finger pressure is applied to the guide, the guide forms a closed space for the needle shaft. The needle is kept with the guide while finger pressure is applied to the guide. In this manner, the guide may be separated from the needle shaft by relieving the finger pressure with little if any unintended movement of the needle shaft while the needle is embedded in a patient.

In one aspect, a needle clip includes a holder forming a cradle for a needle shaft and a cover. The cover is moveable between a first position adjacent the cradle to a second position covering the cradle. A flexible member is connected to the cover and the holder. When the cover is in the second position, the cover and cradle form a closed space adapted for retaining the needle shaft in the cradle, the member is elastically deformed and the cover is devoid of a mechanical engagement with the holder. The flexible member may be a beam or a spring and the cover may be cantilevered from a finger rest, which may connect the flexible member to the cover.

In another aspect, a needle guide includes a holder forming a surface including a cradle adapted to receive a needle shaft and a ledge disposed above and at a first side of the cradle, and a cover having an end. The cover is moveable between a first position located at a second side of the cradle and a second position. When the cover is in the second position, the cover is disposed over the cradle and the end is between the surface and the ledge, the cover and cradle form a closed space adapted for retaining the needle shaft in the cradle and the cover is devoid of a mechanical engagement with the holder. The ledge may be formed by a notch, a U-shaped or C-shaped member formed on the holder. The ledge can function as a surface that restrains separation of the cover from the cradle, e.g., if the needle shaft presses against the cover.

The needle clip may be used with a shell that receives an ultrasound probe. The shell may include structure for attaching the clip to the exterior of the shell, or receiving a connector of the needle clip in an opening of the shell and attaching the connector to a shaft provided with the probe. In the later case, the needle clip may include a sealing member which, when engaged with the opening in the shell forms a sterility barrier with the shell.

The needle guide may be used with a transverse-type or longitudinal-type ultrasound imaging device, and an imaging device that provides a fixed mount and/or adjustable mount for the needle guide.

In another aspect, a method for inserting a needle into a body includes the steps of providing a needle guide on an ultrasound probe, applying finger pressure to the needle guide, wherein the applied finger pressure forms a closed space for retaining a needle shaft in the guide, locating a needle insertion point on the body, inserting the needle shaft into the closed space, inserting the needle into the body, and after the needle is inserted into the body, removing the applied finger pressure so that the needle guide can be separated from the needle shaft.

These and other aspects of the disclosure will become apparent to those skilled in the art after a reading of the following description when considered with the drawings.

DETAILED DESCRIPTION OF THE DISCLOSED EMBODIMENTS

Figure 1:
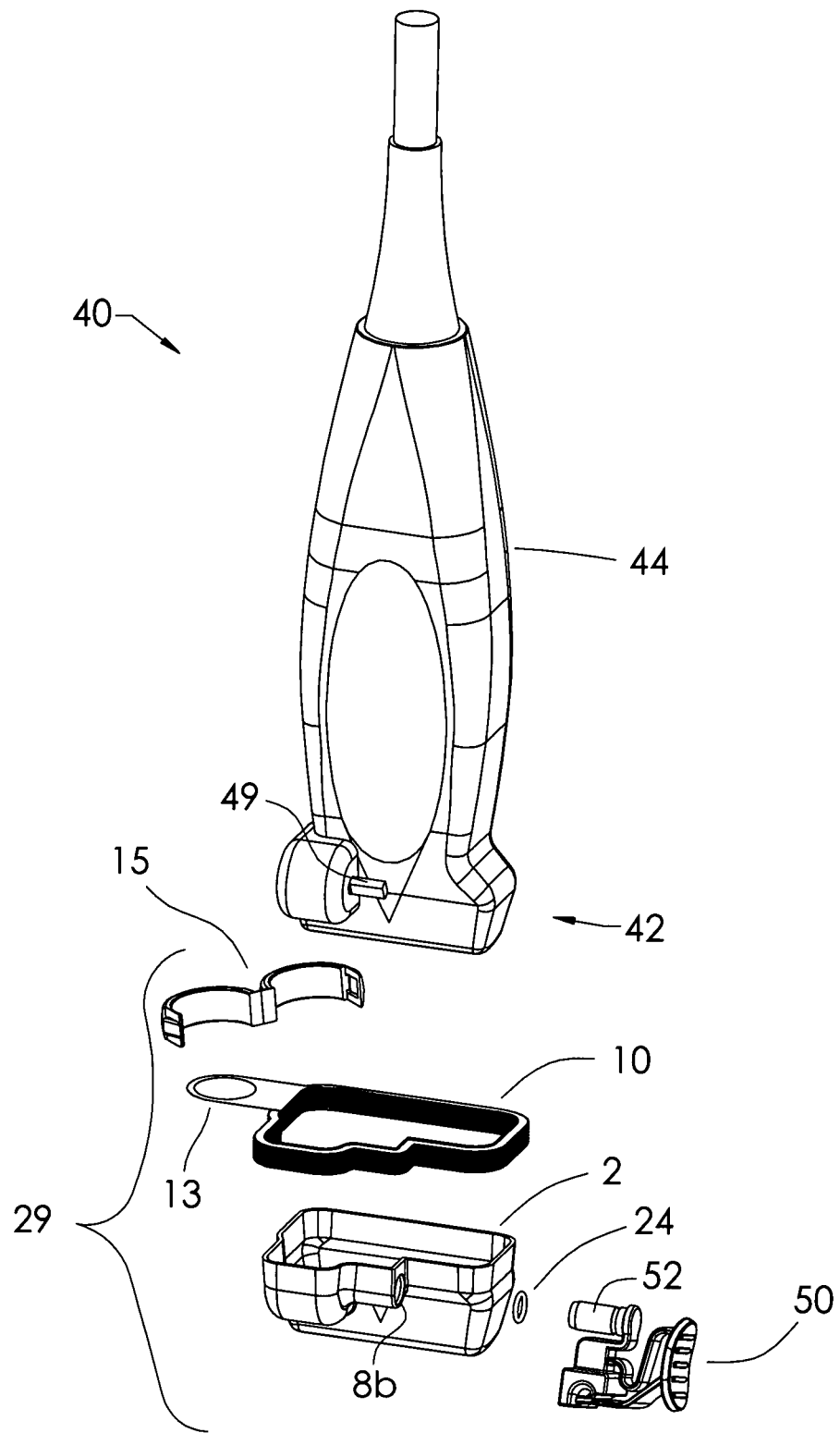
FIG. 1 is an exploded perspective view of an ultrasonic probe and sterile kit for the probe.
Figure 2:
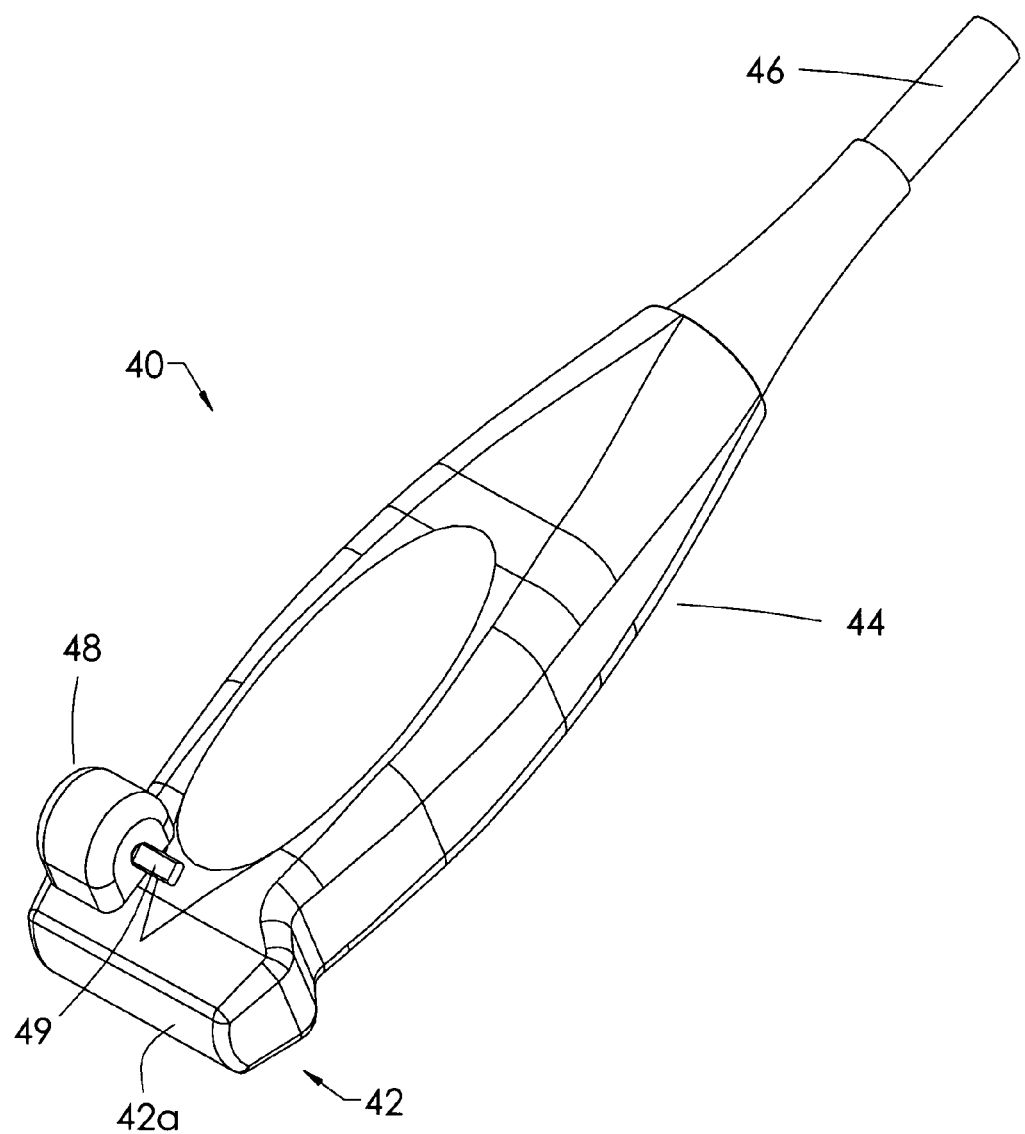
FIG. 2 is a perspective view of the probe of FIG. 1.

FIG. 1 is an exploded perspective view of an ultrasound guidance device according to one aspect of the disclosure. This device includes a sterile kit 29 for use with an ultrasonic probe 40 as in, for example, the ultrasonic probe described in pending U.S. Patent Application Publication No. 2007/0073155, the entire contents of which are incorporated by reference. With reference to FIG. 2, the probe 40 includes a body 44 containing the probe's transducer, a transmitting/receiving end or head 42 which emits and receives ultrasonic signals, a cord 46 for sending ultrasonic images to a nearby monitor (not shown), and a needle positioning and detecting device. The needle and positioning device includes a position encoder (or potentiometer) coupled to a rotatable shaft 49. The position encoder is contained in the portion 48 of the probe body 44 and the shaft 49 protrudes out from this housing 48 so that a needle guide may be received on the shaft 49. An o-ring may be included within the opening for the shaft 49 for sealing purposes. The needle positioning and detector device enables a health professional to reposition a needle held on the probe 40 (via a needle clip received on the shaft 49), rotate that needle through a continuum of angles and track its position relative to a needle target displayed on a nearby monitor.

With reference to FIG. 1, the kit 29 includes a sterile cover 1 and a disposable needle clip 50. The sterile cover 1 includes a shell 2 and a sheath 10 secured to the shell 2. When fully assembled, the head 42 of the probe 40 is placed in the shell 2 and the sheath 10 is pulled or slid over the body 44 and secured thereto by a fastener 15 which may be included as part of the kit 29, see FIG. 5. A connector 52 of the needle clip 50 is then inserted into an opening 8b formed in the shell 2 and connected to the shaft 49 of the needle positioning and detecting device.

Figure 3:
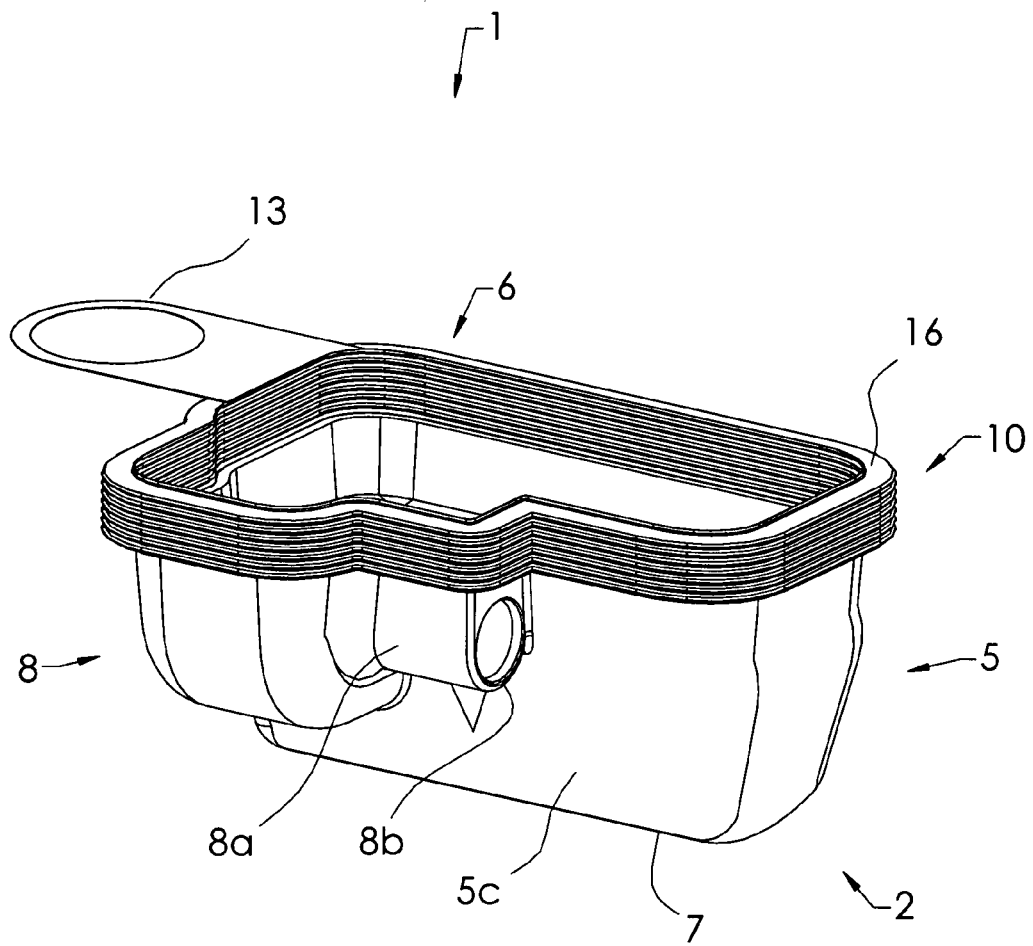
FIG. 3 is a perspective view of a sterile cover of the kit of FIG. 1.
Figure 4:
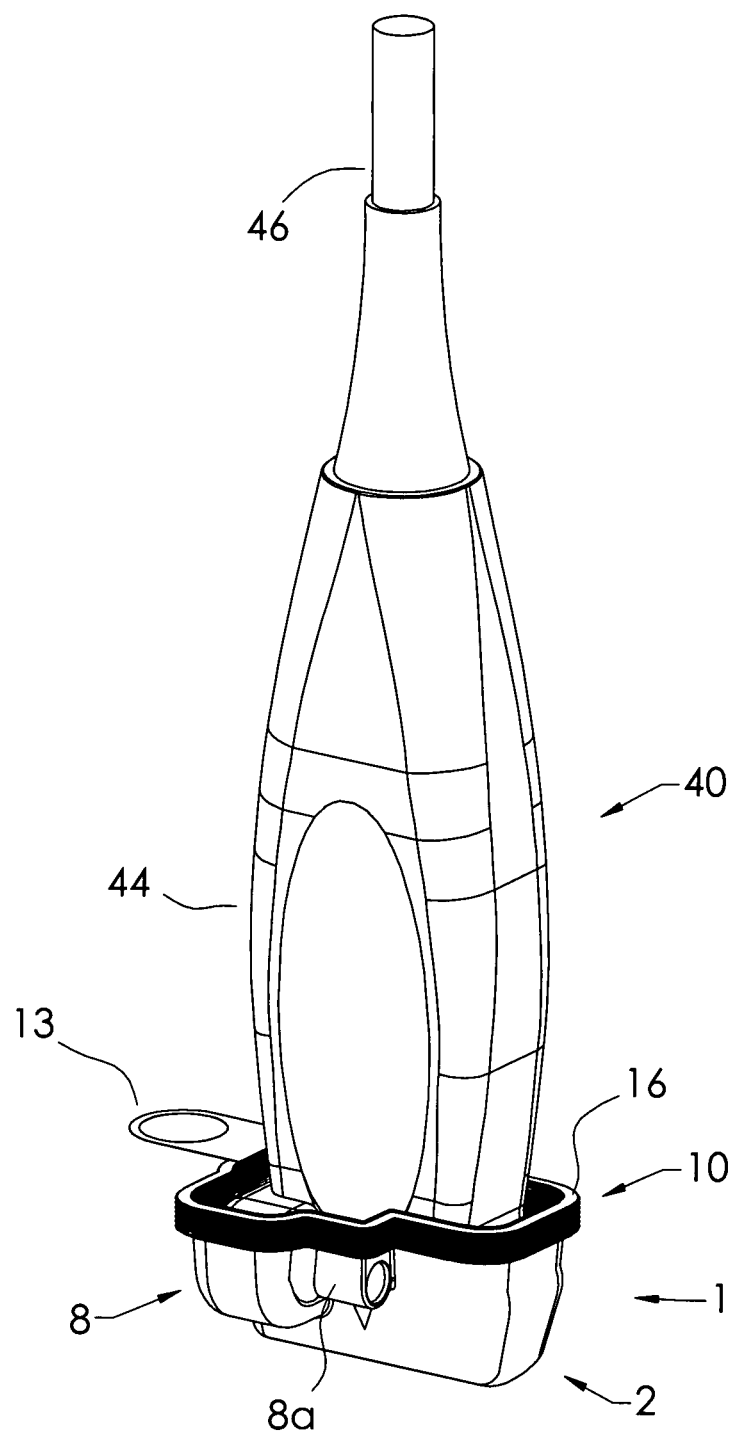
FIG. 4 is a perspective view of the sterile cover of FIG. 3 with a head of the probe received in a shell of the sterile cover.

With reference to FIG. 3, the sterile cover 1 is shown in a stowed or folded configuration. The probe 40 is received in the shell 2, FIG. 4, and then the sheath 10 is pulled over the probe body 44, FIG. 5, and secured by the fastener 15. According to a first disclosure, the sterile cover 1 is sized to receive the probe 40 and hence includes accommodations for the housing 48 of the body 44. The sterile cover 1 may alternatively be formed to enclose various shaped transducer bodies and/or heads, with or without a needle bracket or needle positioning device without departing from the scope of this disclosure.

With reference to FIGS. 1 and 3-6, the shell 2 is preferably formed as a one-piece injection molded part. The head 42 of the probe 40 is received in an interior space 6 of the shell 2. This interior space 6 is formed by an acoustic window 7 and walls 5 which surround the window 7. The walls 5 define an opening 5a at an upper end and tapered portions 5b at opposed sides which extend from the opening 5a to the window 7 and conform to tapered surfaces 42a of the head 42, see FIG. 6. The tapered portions 5b are preferably shaped to provide a snap-fit engagement with the head 42, although the shell 2 may also be formed so that a frictional or elastic press-fit with the head 42 is made. In either approach, the shell—head engagement can be sufficient to ensure that the head 42 is held in place during the ultrasound procedure. This ensures there are no air pockets between the interior surface 5d of the shell 2 and the head surface 42a, which can cause artifacts to appear in the ultrasonic image. When inserted, the head 42 is put in contact with an acoustic coupling gel lining the interior surface 5d of the shell 2. The gel may pre-applied to the interior surface 5d. In this case, a removable lid stock may be applied to the shell opening 5a to protect the gel from contaminates. The gel may also be applied to the surface 5d just prior to inserting the head 42 into the shell 2. The shell 2 may include finger-pressure actuated release areas so that the head 42 may be easily removed from the shell 2. For example, one or more of the walls 5 may include a bulge which, when depressed cause the tapered portions 5b to elastically deflect away from the surfaces 42a of the head 42, thereby releasing the head 42 from the shell 2.

A front wall 5c of the shell 2 may have a section formed to accommodate the housing 48 of the probe's positioning and detecting device. This section includes an extension 8 forming a passage 8a for the needle clip connector 52 and shaft 49, and an opening 8b for receiving the connector 52, see FIG. 10. The opening 8b may include a flexible edge which, when engaged with the clip 50, produces an audible snap fit between an outer sleeve of the clip 50 and walls of the passage 8a so that a user is given an audible confirmation that a tight seal or sterility barrier has been achieved between the connector 52 and the walls of the passage 8a. The sterility barrier may be achieved by over-molding or fitting an o-ring in an annular groove formed in the passage 8a or on the connector 52, or an integrated seal area may be formed in the opening 8b. Alternatively, a sterility barrier may be formed by engaging an annular recess formed within the opening 8b with an annular ridge formed on the connector 52. Preferably, an o-ring 24 is placed on the connector 52, see FIG. 10. The o-ring or sealing structure could be made from any number of elastomeric materials, such as natural rubbers and latex, silicones, polyisoprenes, etc, and may be a purchased component. The o-ring or sealing structure may also be used to provide a desired degree of frictional resistance to rotational movement of the clip 50 during a procedure, in effect functioning as a detent. This may be desirable is it permits a health professional to maintain an angular position of the clip 50 and/or to facilitate precise angular adjustments of the needle clip 50 during a procedure. Since the interfering passage 8a and connector 52 components are intended as single-use only, a desired resistance can be reliably maintained over the life of the product. A detent may alternatively be incorporated into the positioning and detecting device.

The shell 2 may be formed using various semi-rigid polymers such as polypropylene, polyethylene, S—B copolymer, PC-ABS or the like. The material could also be changed to an amorphous material, such as polycarbonate, based on a desired clarity for the ultrasound. The undercut features of the shell 2 may be popped off of the mold, particularly if the plastic is a softer material, such as a polypropylene or polyethylene.

A second component of the illustrated sterile cover 1, the sheath 10, will now be discussed. With reference again to FIGS. 1 and 3-5, the sheath 10 is connected to the shell 2 and adapted for being slid over the body 44 of the probe 40 after the probe 40 has been connected to the shell 2, as depicted in FIG. 5. An upper edge 16 of the sheath may include a pull tab 13 that is used to pull the sheath 10 over the probe body 44. The sheath 10 may be formed from a thin, extruded material, such as a polyethylene, polyurethane, or similar film material, which can be pre-folded, preferably in an accordion-like fashion. The sheath may also be dip molded. The sheath may be considered as the flexible part of the sterile cover 1 and the shell 2 the rigid part.

Figure 5:
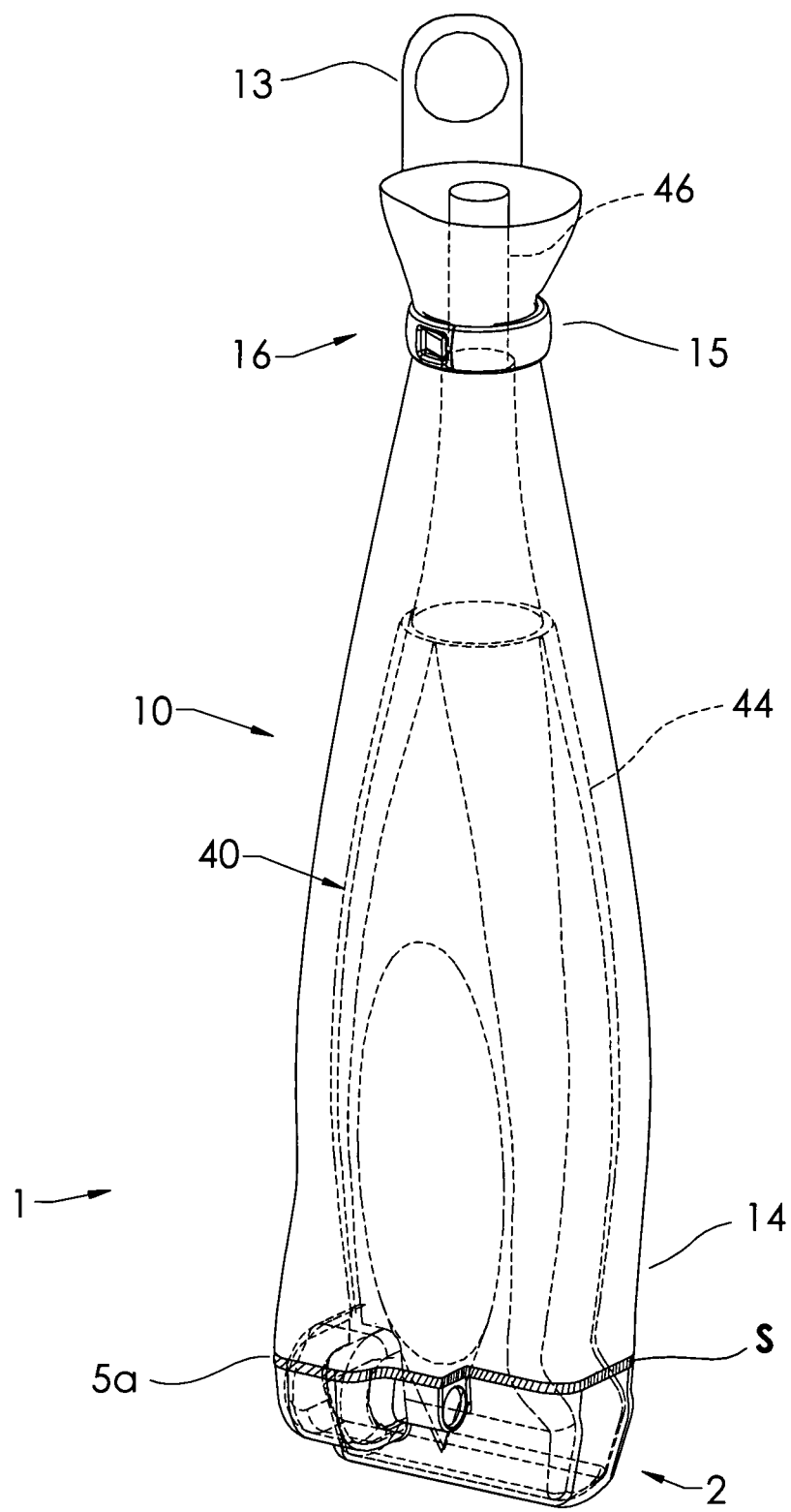
FIG. 5 is a perspective view of the sterile cover and probe of FIG. 3 with a sheath of the sterile cover covering the probe.

Referring to FIG. 5, which shows the probe 40 enclosed within the sterile cover 1, a bottom edge 14 of the sheath 10 is sealed to the shell 2 by a seal s along the entire perimeter of the opening 5a. The upper edge 16 of the sheath 10 extends up to the cord 46 and is secured thereto by the fastener 15, e.g., a C-clip (a fastener may be secured to the sheath 10 so that it may be used to both pull the sheath 10 over the probe and secure the sheath 10 to the cord 46). The seal s may be formed by solvent bonding of the edge 14 to the opening 5a. A heat seal, sonic or RF weld or other methods may be used. These connection methods may serve not only the purpose of securely retaining the sheath 10 to the shell 2, but also forming a consistent seal along the entire perimeter of the opening 5 to ensure that sterility is maintained. An effective connection and sterility barrier may also be provided by a seal formed from a press fit between the opening 5a and the lower edge 14. In such a case, the opening 5a may include along its perimeter a channel or groove that receives, via a press-fit, a flexible rim disposed along the perimeter of the lower edge 14 of the sheath 10. With reference again to FIG. 5, when the sheath 10 is fully deployed and the fastener 15 secured as shown, the only passageway between the interior of the sterile cover 1 and the external environment is at the opening 8b, which receives the clip connector 52.

Figure 6:
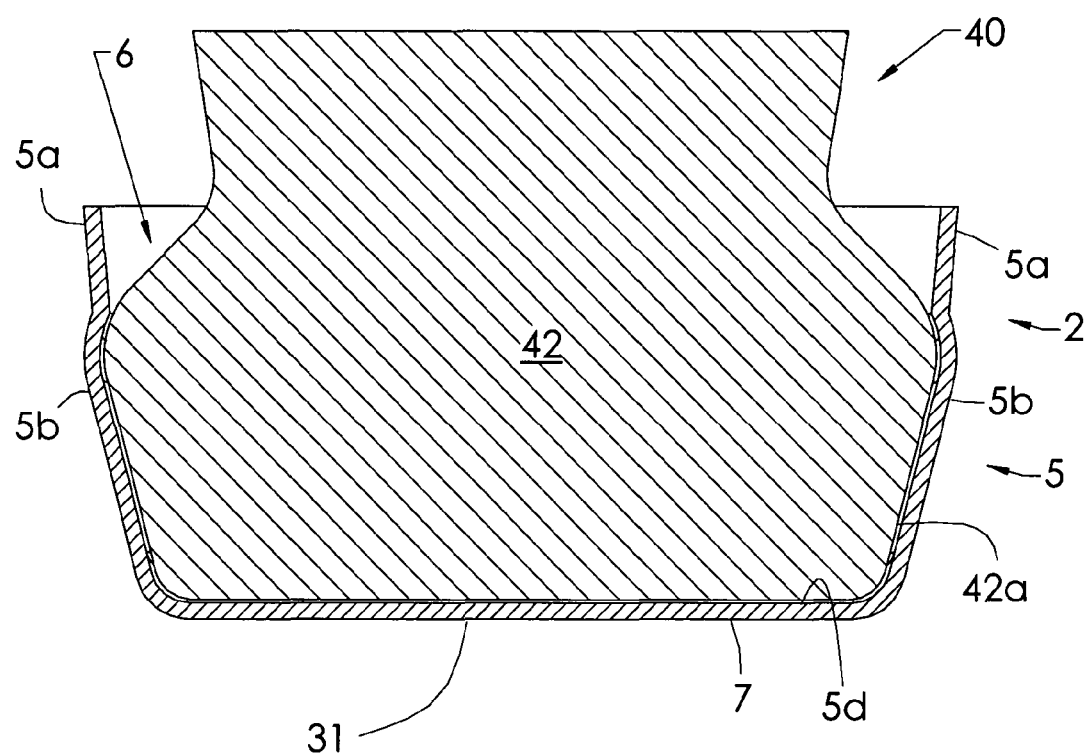
FIG. 6 is a partial side cross-sectional view of the probe with the head connected to the shell.

A procedure for assembling the ultrasonic device of FIG. 1 will now be discussed. The kit 29, containing the sterile cover 1 and one or more needle clips 50, is removed from a sterile packaging. The acoustic coupling gel may be provided with the kit 29 and applied directly to the interior 6 of the shell 2. Preferably, the gel is already present within the shell and protected from contaminates by a hermetic seal, e.g., a lid stock covering the opening 5a of the shell 2. The lid stock is removed from the shell and the head 42 of the probe 40 snap-fit into the shell 2, thereby forming a consistent acoustic medium between the face 42a of the head 42 and the window 7 of the shell 2 for sound transmission (FIG. 6). The pull tab 13 is then used to slide the sheath 10 over the body 44 of the probe and the fastener 15 secures the sheath 10 to the cord 46. The connector 52 of the sterile clip 50 is then inserted into the opening 8b of the shell 2. At this point, the ultrasonic device is sterile and ready for use.

The embodiments of the sterile cover 1 thus described are preferably intended for use with an ultrasonic probe equipped with an adjustable needle guide feature, e.g., the ultrasonic probe described in pending U.S. Patent Application Publication No. 2007/0073155. However, it will be understood from the foregoing that other embodiments of the sterile cover 1 are within the scope of this disclosure. The sterile cover 1 may be constructed for use with a probe that uses a longitudinal-type needle positioning and guidance device or a probe that does not use a needle guide. In these cases, the shell 2 and sheath 10 would be formed with an opening located on the side of the shell 2 or without accommodations for receiving a needle clip on the probe, respectively. In other embodiments, the shell 2 may include a bracket for a mounting a needle clip.

Figure 7:
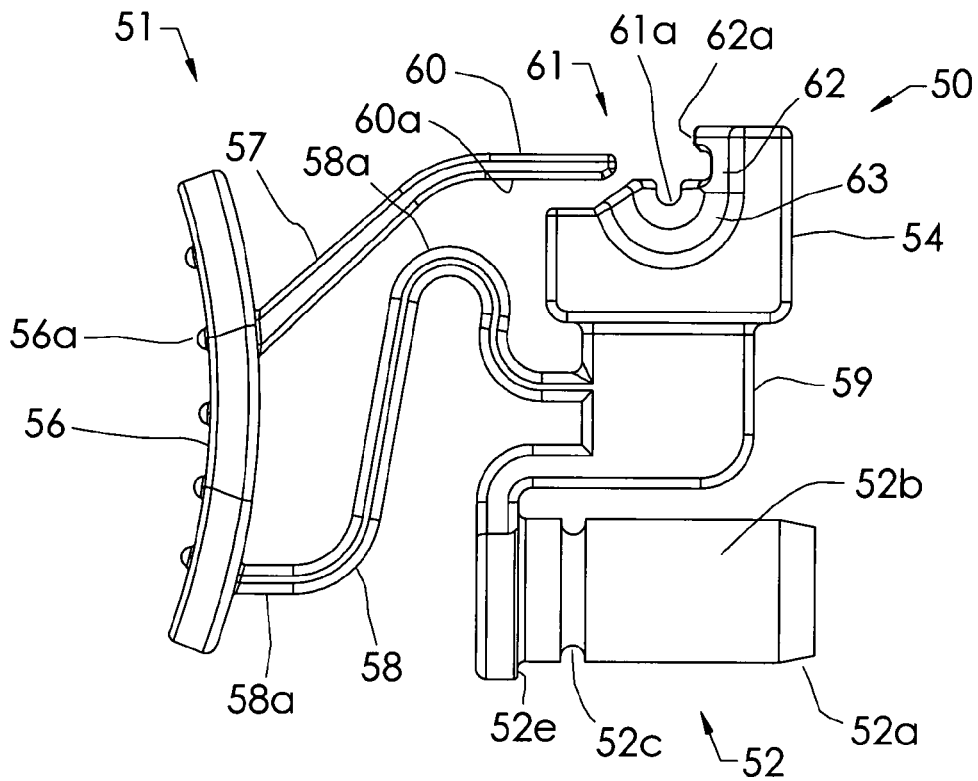
FIGS. 7 and 8 are side and perspective views, respectively of a needle clip of the kit of FIG. 1.
Figure 8:
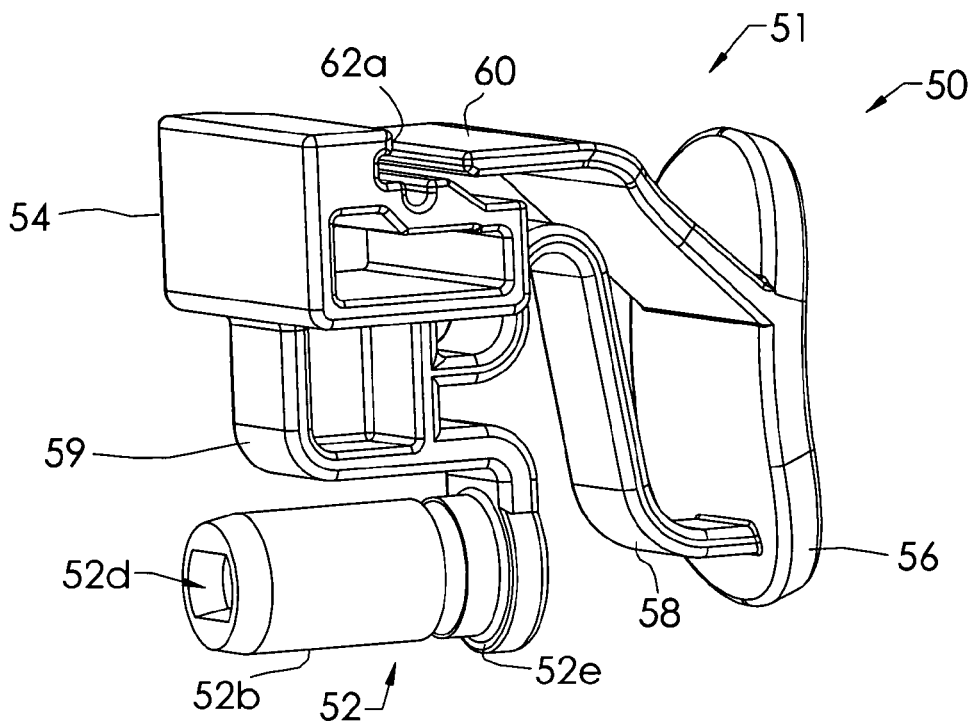

Reference will now be made to embodiments of the needle clip 50. During the course of this description, the features of the clip 50 will be described with reference to its preferred use with the probe 40. However, It will be understood that the needle clip 50 may be used with other probe types. The needle clip 50 is constructed so that the needle shaft may be separated from the probe with little unintended movement of the needle shaft while the needle shaft is embedded within the patient. FIGS. 7 and 8 illustrate two views of the needle clip 50 according to a first disclosure. The needle clip 50 may be formed as a single-piece molded part forming a holder 54 for a needle shaft and a supporting post 59 connecting the holder 54 to the connector 52. The needle holder 54 includes a semi-circular track or cradle 61a which receives the needle shaft. An engaging portion 51 of the needle clip 50 operates to retain the needle shaft in the cradle 61a. The engaging portion 51 includes a finger rest 56 having ridges 56a which provide a gripping feature, a flex member 58 and a fastening arm 57 having a cover 60 portion disposed adjacent to the cradle 61a.

Figure 10:
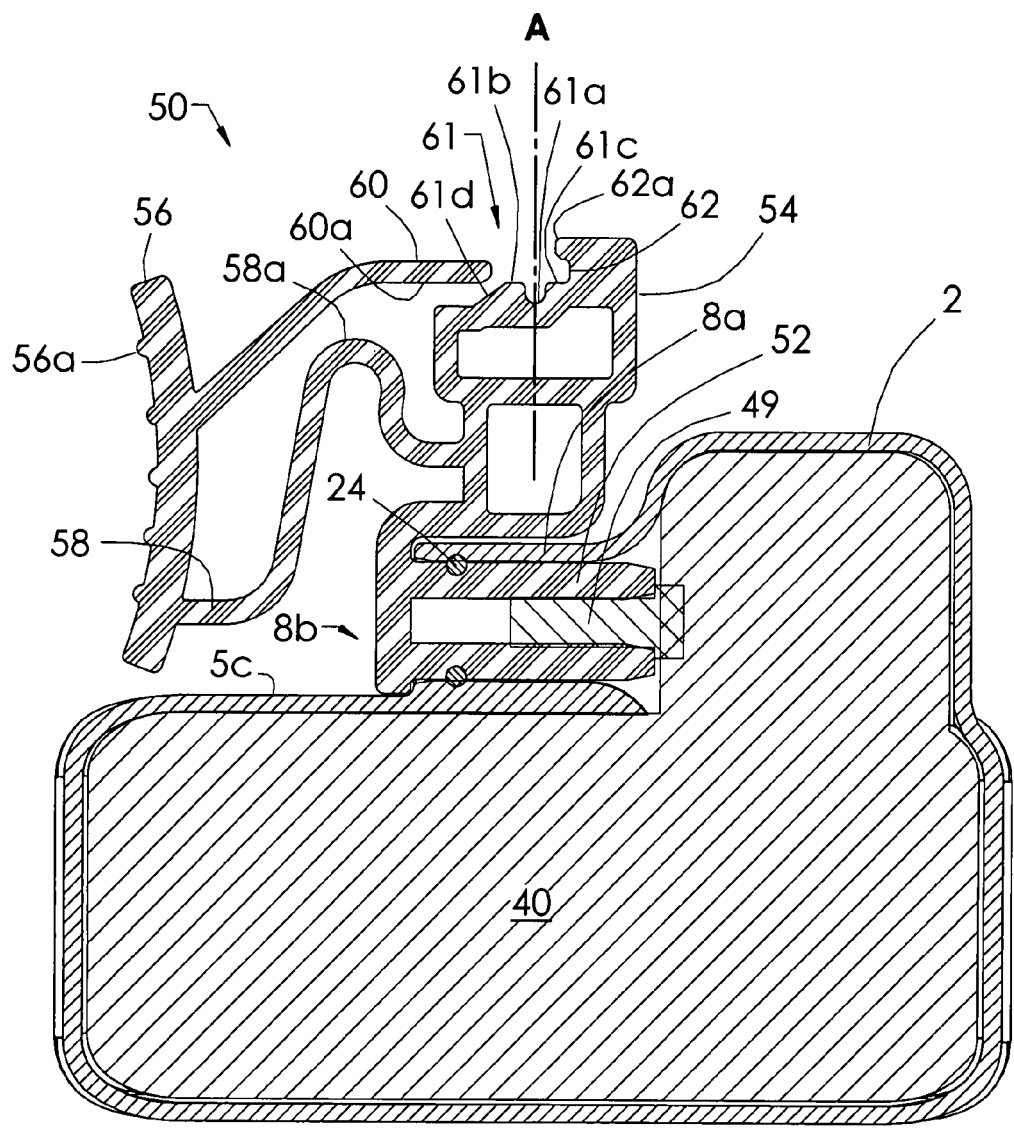
FIG. 10 is a partial top cross-sectional view of the needle clip, sterile cover and probe of FIG. 9.
Figure 11:
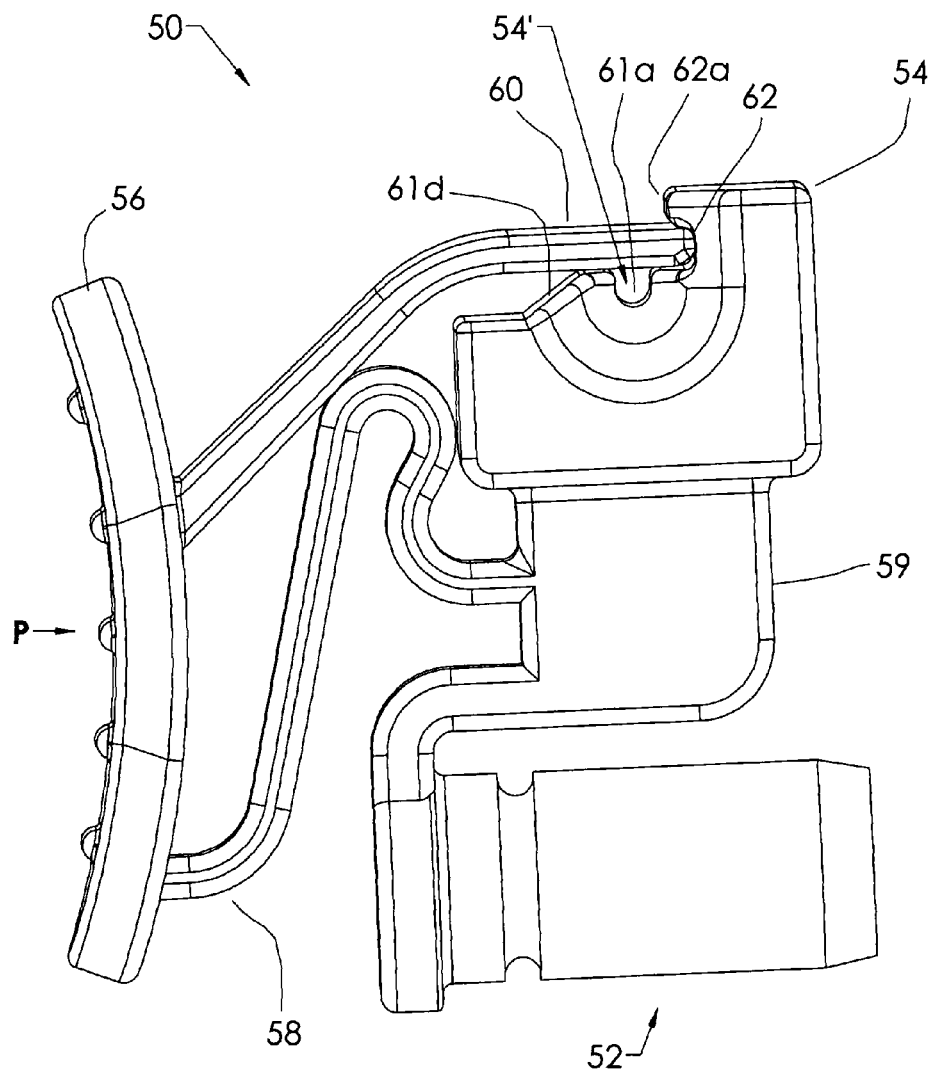
FIG. 11 is a side view of the needle clip of FIG. 7 with finger pressure applied to the needle clip.

The engaging portion 51 operates in the following manner. When the needle shaft is received in the cradle 61a, the operator, i.e., a health professional, applies finger pressure to the finger rest 56 causing displacement of the cover 60 towards the right in FIG. 7 until the cover 60 is received in a notch 62 of the holder 54 (FIG. 11). Specifically, as finger pressure is applied, the cover 60 passes over a surface 61 which includes flat surfaces 61b and 61c on left and right sides of the cradle 61a. A sloped surface 61d guides the cover 60 leading edge towards the cradle 61a (FIG. 10). The cover 60 is then received in the notch 62. A lower surface 60a of the cover 60 is now adjacent the surfaces 61b and 61c, and the portion of the surface 60a over the cradle 61a forms a closed space 54' with the cradle 61a. The closed space 54' may be thought of as a needle passageway or needle track. One or more chamfers 63 may be formed on the holder 54 to assist with guiding a tip of the needle into the cradle 61a. FIG. 11 illustrates the position of the cover 60 when finger pressure p is applied to the finger rest 56 and FIG. 7 illustrates the position of the cover 60 when there is no finger pressure applied.

The flex member 58, which may take a serpentine shape having at least one bend 58a, is attached to the finger rest 56 at a first end and to the supporting post 59 at the opposite end thereof. The flex member 58 may be replaced by a compression spring. When finger pressure is applied to the finger rest 56, the flex member 58 is elastically deformed and the cover 60 deflects into the notch 62 (FIG. 11). And when finger pressure is relieved, restoring forces in the flex member 58 withdraw the cover 60 from the notch 62 and return the cover 60 to the position shown in FIG. 7. The fastening arm 57 is sloped upwards to promote a deflection of the cover 60 into the notch 62 when finger pressure is applied. In other embodiments, the needle clip 50 may be configured so that a tension spring or a torsion spring is used in place of the illustrated flex member 58, which functions as a compression spring.

Figure 9:
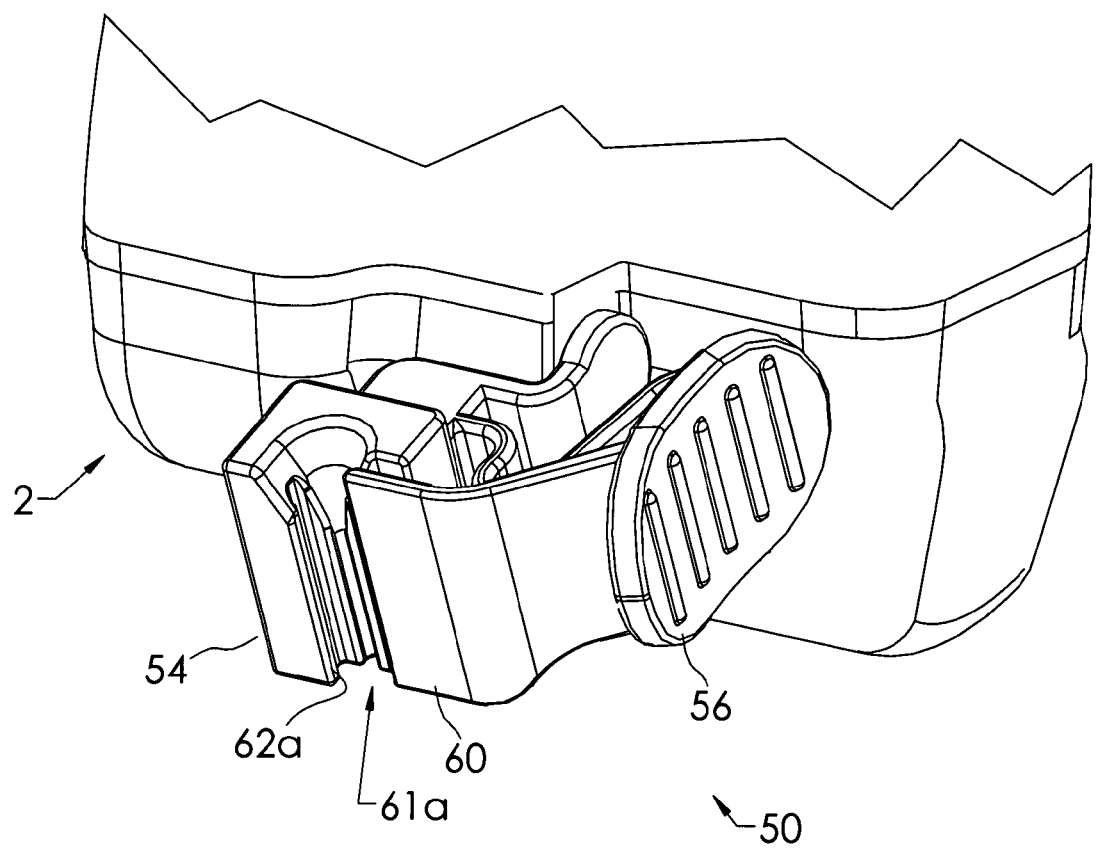
FIG. 9 is a partial perspective view of the sterile cover and probe of FIG. 5 with the needle clip of FIG. 7 connected to the shell.
Figure 13:
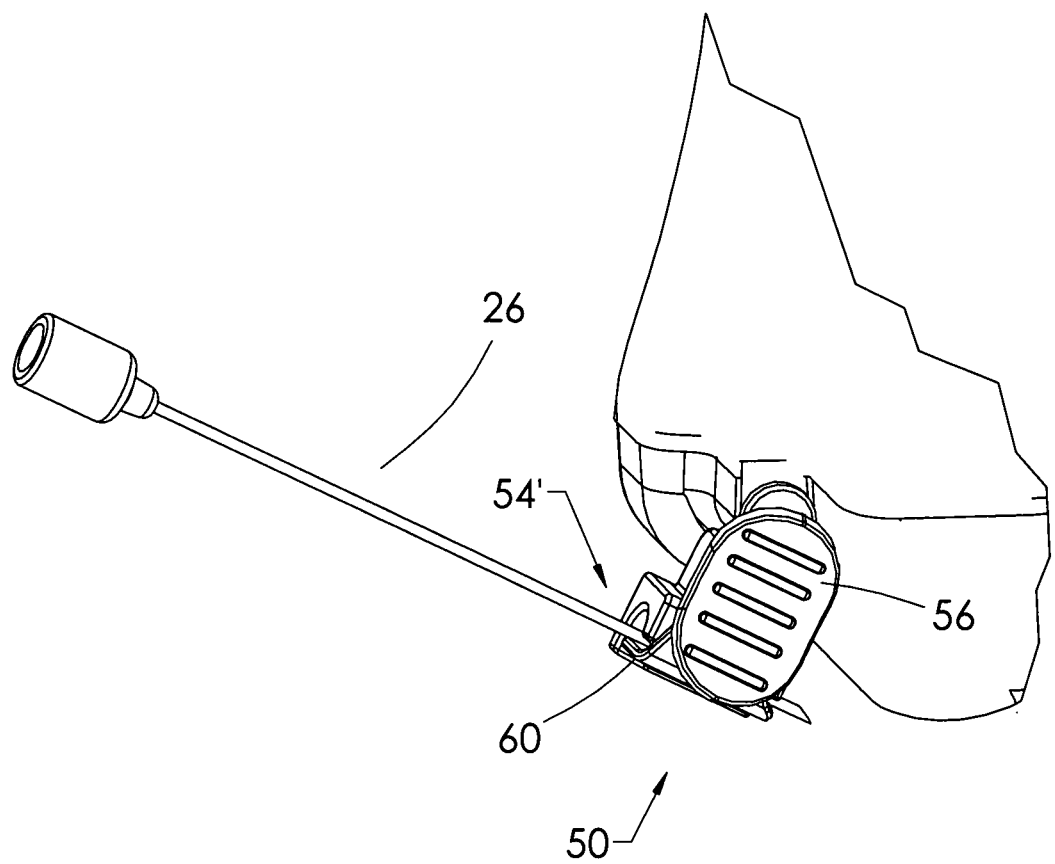
FIG. 13 is a perspective view of the needle shaft of FIG. 12 retained in the needle clip.

With reference to FIG. 11, a needle shaft received in the space 54' is restrained from inadvertent dislodgement from the cradle 61a. The surface 60a and the surface of the cradle 61a may form the closed space 54' to hold the needle shaft in place. The space 54' may be a substantially closed space, e.g., the surface 60a and surfaces on either side of the cradle 61a do not abut each other, since this closed space may also prohibit unwanted movement of the needle shaft. The space 54' is maintained only when finger pressure is applied to the finger rest 56. Hence, the needle clip 50 is devoid of a mechanical fastener or engagement between the cover 60 and the needle holder 54. When the finger pressure is released from the finger rest 56, the cover 60 naturally withdraws from the cradle 61a by the restoring forces inherent in the compressed flex member 58. The needle clip 50 and probe 40 are thus allowed to separate from a needle shaft embedded in a patient by simply removing one's finger from the finger rest 56. A perspective view of the needle clip 50 attached to the shell 2 of the sterile probe 40, when there is no finger pressure applied to the finger rest 56, is shown in FIG. 9. FIG. 13 shows a needle shaft 26 received in the space 54' when finger pressure is applied to the finger rest 56.

The needle clip 50 may include structure that aids in preventing separation between the cover 60 and the surface 61. A separation may be caused by excessive finger pressure applied to the finger rest 56 or movement of a needle shaft which tends to force the surfaces 60a and 61 apart from each other. If a resulting space is formed between the surfaces 60a and 61, the needle shaft may become dislodged from the cradle 61a. To address these situations, a ledge 62a extending from the notch 62, may be formed adjacent and above the cradle 61a. By positioning the ledge 62a in this manner, the cover 60 leading edge will have less tendency to deflect away from the surface 61. The leading edge of the cover 60, notch 62 and/or ledge 62a may include cooperating beveled edges to assist with guiding the cover 60 into the notch 62. In alternative embodiments, the notch 62 and/or ledge 62a may be provided by a passage, hole or c-shaped member sized to receive the leading edge of the cover 60.

With reference again to FIGS. 7, 8 and 10, the connector 52 is preferably configured to connect with the shaft 49 of the probe 40. The connector 52 may be cylindrical, having an interior passage 52d which may be configured to receive a rectangular, rotatable shaft 49 of the probe 40. The exterior wall 52b of the connector 52 is formed to slide along corresponding walls of the passage 8a of the shell 2. Preferably, the connector 52 includes an annular recess 52c which receives the sealing o-ring 24. As discussed earlier, the o-ring 24 may provide a sterility barrier with the walls of the passage 8a, as well as a detent feature for the needle clip 50. When the connector 52 is fully inserted into the opening 8a and engaged with the shaft 49, an end 52e of the connector 52 abuts with the opening 8b of the shell 2. The connector 52 may include a lead-in chamfer 52a to aid with its positioning in the opening 8b. FIG. 10 illustrates a top cross-sectional view of the clip 50 received on the shaft 49.

The connector 52 may include an elastic edge or recess that snaps into a mating recess or ridge, respectively of the shaft 49 to confirm that the connector 52 is properly received on the shaft 49. The engagement may be such that an audible confirmation is provided when proper engagement is achieved, e.g., by a "clicking" sound. This confirmation may be desirable for the purpose of giving assurance that the needle shaft, when received on the cradle 61a, is aligned with a reference axis A (see FIG. 10) of the probe's positioning and detecting device. For example, in the ultrasonic guidance system described in pending U.S. Patent Application Publication No. 2007/0073155, a needle tracking feature may produce a visual image of a needle's position relative to an ultrasonic image, as well as its pathway intersecting the image plane as the needle is rotated relative to the probe 40. Assuming the cradle 61a and hence the needle shaft is positioned on the axis A, the displayed needle position reflects the true position of the needle shaft relative to the image plane.

Figure 12:
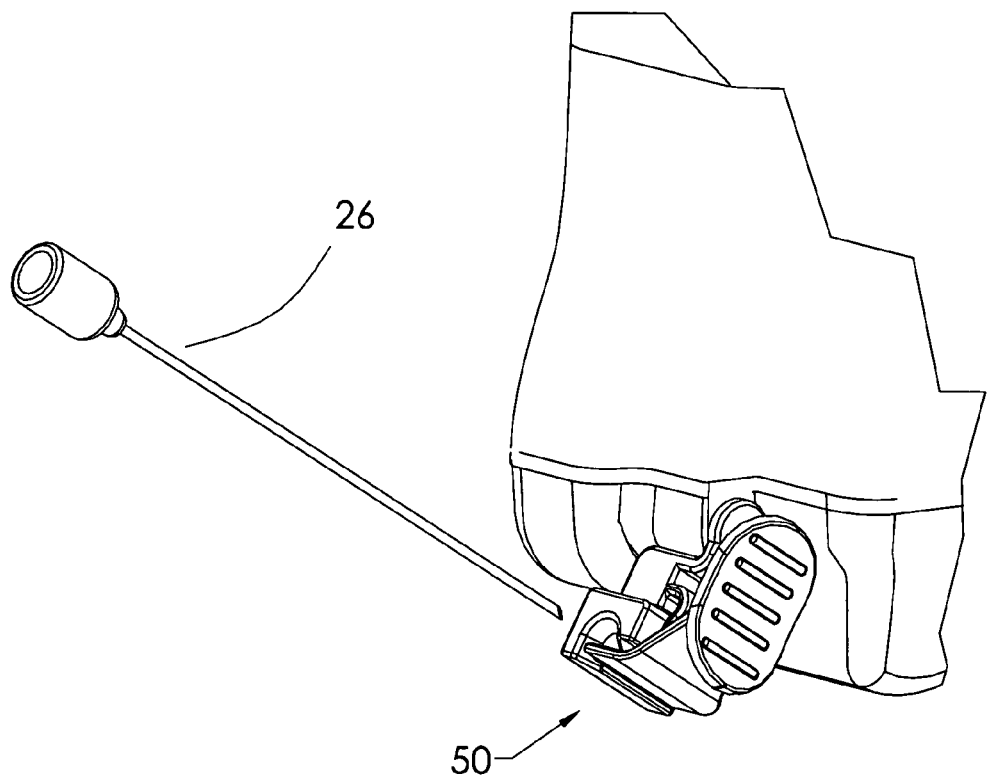
FIG. 12 is a perspective view of a shaft of a needle positioned for insertion into the needle clip.
Figure 14:
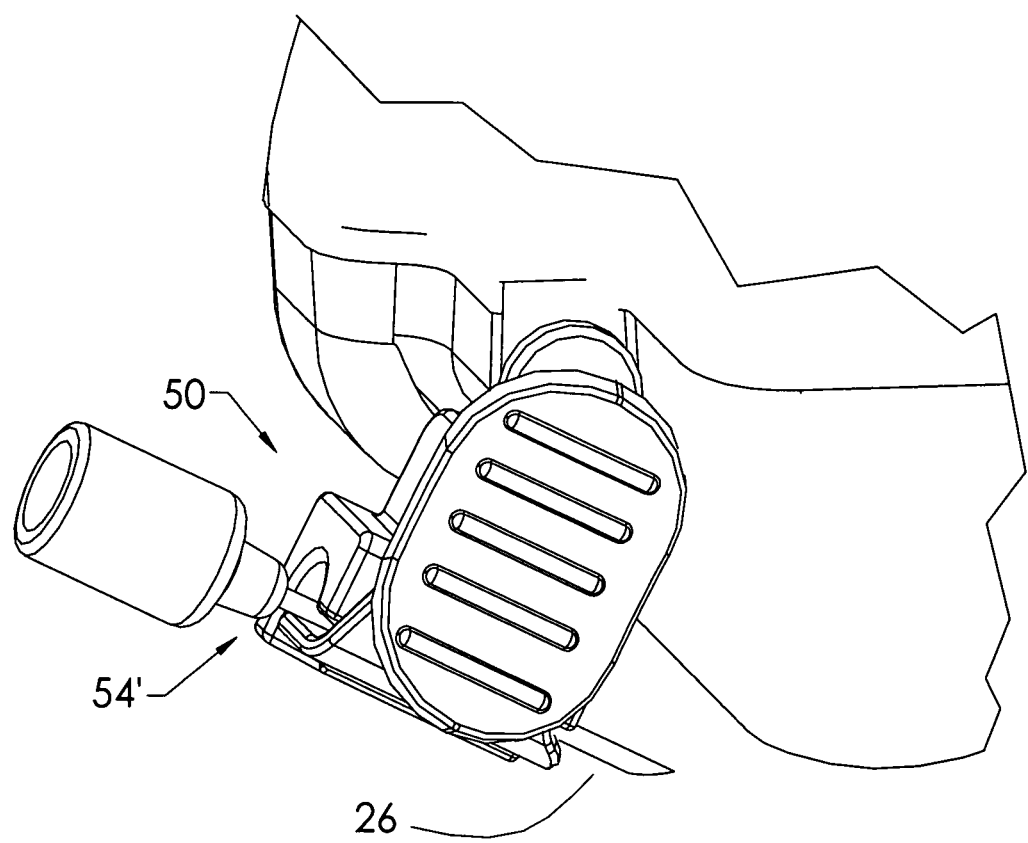
FIG. 14 is a perspective view of the needle shaft of FIG. 12 when embedded in a patient.
Figure 15:
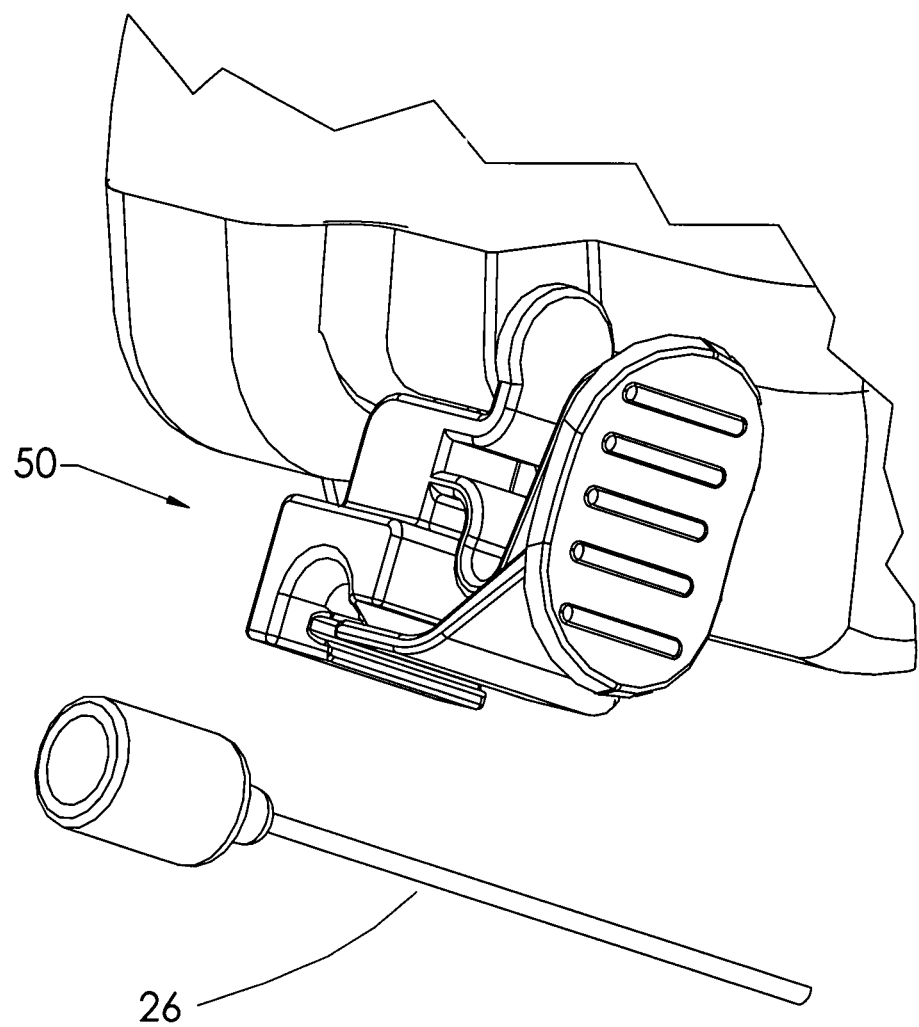
FIG. 15 is a perspective view of the needle clip after it has been separated from the embedded needle of FIG. 14.

In a medical procedure, the needle clip 50 may be used to locate and insert a needle into a body of a patient using the probe 40 in the following manner. With the needle clip 50 attached to the shaft 49 of the probe 40, the health professional first locates a desired needle pathway by rotating the clip 50 relative to the probe 40. With the aid of a monitor, the movement of the needle clip and hence a needle pathway into the body may be visualized with respect to the ultrasonic image of the interior of the body, e.g., in the manner described in pending U.S. Patent Application Publication No. 2007/0073155. The clip 50 may be configured so that when the clip 50 is being rotated into position, the applied finger pressure also places the cover 60 over the cradle 61a, thereby forming the closed space 54'. When the correct needle pathway is found, the needle shaft 26 is inserted into the space 54' (FIGS. 12 and 13), and then into the patient (FIG. 14). After the needle shaft 26 has been successfully located at the target, the finger pressure is removed from the needle clip 50, causing the cover to withdrawn from the cradle 61a. The probe 40 is now easily removed from the needle shaft without additional steps needed to free the needle clip 50 from the embedded needle shaft 26 (FIG. 15).

In other embodiments, the connector 52 may be replaced by fastening structure suitable for use with other types of probes. In the case of an ultrasound imaging probe that includes a fixed-position needle clip bracket, the clip 50 may be easily configured to mount to structure provided on the exterior of a sterile shell or elsewhere, e.g., a post, sleeve, groove, etc. Additionally, the connector 52 may be configured so that it can be used with a longitudinal type ultrasound guidance system having either an adjustable or fixed needle guide feature. Also, the embodiments of a needle clip set forth in pending U.S. Patent Application Publication No. 2007/0073155 may be readily adapted for use in accordance with one or more of the foregoing embodiments.

What we claim is:

1. A needle guide, comprising:
 a support comprising a cradle configured to receive a needle shaft;
 a finger rest;
 a cover attached to the finger rest;
 a flex member having a first end connected to the finger rest and a second end connected to the support, wherein the flex member is elastically deformable between the first end and the second end;
 in a first position, the flex member is not elastically deformed and the cover projects toward the cradle;
 in a second position, the flex member is elastically deformed between the first end and the second end, the cover covering the cradle;
 wherein the flex member in the second position provides a restoring force, the restoring force naturally withdrawing the cover from the second position covering the cradle back to the first position uncovering the cradle; and
 a cylindrical connector coupled to the support configured for being rotatably received;
 and
 wherein the needle guide is a one-piece molded part.

2. The needle guide of claim 1, wherein the flex member is a beam with at least one bend.

3. The needle guide of claim 1, further comprising a sterile shell assembly receiving the connector.

4. The needle guide of claim 1, wherein the cover is a cantilever.

5. The needle guide of claim 1, further comprising a position encoder of an ultrasonic probe connected to the connector.

6. The needle guide of claim 1, wherein the spring is one of a compression spring, a torsion spring, or a tension spring.

7. A needle guide kit, comprising:
 (i) a needle clip as defined in claim 1;
 and
 (ii) a shell rotatably received by the connector and configured for being coupled to an ultrasound probe.

8. The needle guide kit of claim 7, the cradle including a surface and a ledge disposed at a first side of the cradle, wherein the surface includes flat surfaces formed at the first and second sides of the cradle.

9. The needle guide kit of claim 8, wherein the cradle includes a notch comprising the ledge.

10. The needle guide kit of claim 9, wherein an end of the cover is received in the notch when the cover is in the second position.

11. The needle guide kit of claim 7, wherein the cover is maintained in the second position only when external pressure is applied to the finger rest.

12. The needle guide kit of claim 7, wherein the member is a passage and the connector is receivable in the passage, the kit further comprising a sealing member in the passage or on the connector providing a sterility barrier.

13. The needle guide kit of claim 7, wherein the shell has a cylindrical passage rotatably receiving the connector, and comprising a sealing member in the cylindrical passage or on the connector forming a sterility barrier with the shell.

* * * * *